(12) United States Patent
Florin et al.

(10) Patent No.: US 8,597,909 B2
(45) Date of Patent: Dec. 3, 2013

(54) USE OF HSA-PRODUCING CELLS

(75) Inventors: Lore Florin, Biberach (DE); Rebecca Bischoff, Warthausen (DE); Juergen Fieder, Biberach (DE); Hitto Kaufmann, Ulm (DE); Thomas Krieg, Warthausen (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 69 days.

(21) Appl. No.: 13/062,781

(22) PCT Filed: Sep. 9, 2009

(86) PCT No.: PCT/EP2009/061679
§ 371 (c)(1),
(2), (4) Date: May 3, 2011

(87) PCT Pub. No.: WO2010/029101
PCT Pub. Date: Mar. 18, 2010

(65) Prior Publication Data
US 2011/0262967 A1   Oct. 27, 2011

(30) Foreign Application Priority Data
Sep. 10, 2008  (EP) .................................. 08164053

(51) Int. Cl.
*C12P 21/06*  (2006.01)
(52) U.S. Cl.
USPC ..................................................... 435/69.1
(58) Field of Classification Search
USPC ..................................................... 435/69.1
See application file for complete search history.

(56) References Cited

U.S. PATENT DOCUMENTS 8,221,999 B2 *  7/2012  Kaufmann et al. .......... 435/69.1

FOREIGN PATENT DOCUMENTS

WO    2006047380 A2    5/2006

OTHER PUBLICATIONS

International Search Report and Written Opinion for PCT/EP2009/061679 mailed Nov. 26, 2009.
Shani, M. et al., "Expression of human serus albumin in the milk of transgenic mice". Transgenic Research 1, Vo. 51, No. 5, Sep. 1992, p. 195-208.
Calvo, Fabien et al. "Continuous Culture and Soft Agarose Cloning of Multiple Human Breast Carcinoma Cell Lines in Serum-free Medium", (1984) Cancer Research, vol. 44, pp. 4553-4559.

* cited by examiner

*Primary Examiner* — Karen Cochrane Carlson
(74) *Attorney, Agent, or Firm* — Michael P. Morris; David L. Kershner; Usha R. Patel (57) ABSTRACT

The present invention refers to the area of cell culture technology and relates to methods for multiplying/cloning cells, preferably cell lines, which are important to the production of biopharmaceuticals. The invention further relates to methods for manufacturing proteins and to the use of cells extracted and multiplied through single cell sorting and to media compositions that enable a multiplication of single cells. Through the use of albumin-producing, preferably HSA-producing, cells as feeder cells for the conditioning of medium or as host cells, the recloning efficiency and thereby the quantity of clones obtained can be significantly increased. A combination of these approaches is also possible. Through the use of albumin-producing, preferably HSA-producing, cells, an increase in the recloning efficiency can be achieved in serum-free and/or insulin-free medium as well, and in different cell types.

16 Claims, 7 Drawing Sheets

USE OF HSA-PRODUCING CELLS

BACKGROUND TO THE INVENTION

1. Technical Field

The present invention relates to the field of cell culture technology and relates to methods of replicating/cloning cells, preferably cell lines which are important for the production of biopharmaceuticals. The invention also relates to methods of preparing proteins using cells that have been obtained and replicated and compositions which makes it possible to replicate individual cells.

2. Background

The market for biopharmaceuticals for treating humans is growing fast throughout the world. Over 900 biopharmaceuticals are currently being tested in clinical trials with an estimated potential turnover of 50 billion in 2010 (Datamonitor 2007). At present, an ever increasing number of biopharmaceuticals are produced in mammalian cells, as these have the capability for the correct processing and modification of a human protein. The successful production of high yields of biopharmaceuticals in mammalian cells is therefore crucial and depends on the characteristics of the recombinant monoclonal producing cell line that is used in the manufacturing process. In addition the duration of the cell line development is a critical time factor as to how quickly the biopharmaceutical can enter into clinical trials. In view of these aspects there is an urgent need to speed up the process of developing cell lines and make it more efficient.

For the biotechnological production of biologically active or therapeutic proteins in mammalian cells, so-called biopharmaceuticals, the corresponding mammalian cells are stably transfected with DNA which codes for the biologically active protein (or its subunits). After the transfection process a pool of millions of differently transfected cells is normally obtained. Therefore the crucial step for the preparation of efficient production cell lines is in the selection and replication of cell clones which on the one hand grow very stably and on the other hand show a high specific productivity of therapeutic protein (product formation etc.). As there are millions of different product-expressing cells, it is critical to be able to analyse a plurality of cells individually with a high throughput and using automation in order to be able to sort out suitable candidates (single cell clones) which both grow very robustly and also yield high product titters. This process of single cell isolation and subcultivation is known as cloning or recloning.

The use of animal cell cultures for producing biopharmaceuticals demands a genotypically and phenotypically homogeneous, i.e. monoclonal cell culture. This is achieved by recloning techniques such as "limited dilution" or by the automated depositing of individual cells by fluorescence activated cell sorting (FACS).

However, there is the problem of effectively replicating typical recombinant production cells such as mouse myeloma (NS0), hamster ovary (CHO), or hamster kidney cells (BHK), particularly if they are adapted to growth in serum-free suspension cultures, i.e. under modern production-relevant cell culture conditions, after recloning, whereby the cells are individually deposited in microtitre plates, under serum-free culture conditions.

The reason for this is that cells in vivo are embedded in the tissue matrix and are supplied with secreted auto- and paracrine growth factors by adjacent cells. They are therefore not adapted to isolated growth and die off without stimulation by growth factors if they are not slowly adapted to the new conditions.

In particular, the use of serum-free or chemically defined media in the recloning step leads to a restricted recloning efficiency, i.e. only a small percentage of the cells deposited survive and grow into a monoclonal cell line.

The "limited dilution" and FACS recloning techniques currently used are well known in the art.

In "limited dilution" the cell suspension is serially diluted and the cells are then deposited in a microtitre plate in different numbers of cells per well. In wells containing large numbers of cells, many or all the cells survive as the result of adequate secretion of autocrine growth factors. The fewer cells are seeded per well, the fewer cells survive, so that in this way the dilution can be adjusted so that statistically only one cell survives per well and grows into a monoclonal line. These individual cells clones are detected by visual and/or imaging techniques and the cell clones are grown on in larger culture vessels.

In FACS technology, a flow cytometer is used to generate single cell clones. For this the cells are placed in a laminar flow and are individually steered into the wells of the microtitre dishes. This ensures that the surviving colonies really are individual clones. Therefore, FACS technology is the preferred method compared with Limited Dilution.

The use of serum-free or chemically defined media in the recloning step leads to restricted recloning efficiency, i.e. only a few percent of the individually deposited cells grow into a monoclonal cell line.

At a low recloning efficiency, therefore, a number of microtitre plates have to be filled with single cells in order to obtain the desired number of individual clones, which is time-consuming and expensive (e.g. in terms of media, dishes, etc).

A low recloning efficiency is particularly disadvantageous if the subsequent analysis of the single cell clones is to be carried out using an automated system. A analysing robot cannot normally distinguish between wells containing living or dead cells and automatically measures all the wells in the microtitre plate. With a recloning efficiency of only 10%, this means that in 90% of cases the robot will analyse an empty well—and will use the same amount of reagent for this as for analysing a living cell clone. In the example here, therefore, 90% of the time and 90% of the material costs are wasted without any data being obtained.

To solve this problem, in the past, serum (e.g. foetal calf serum, FCS) has often been added to the medium. Serum contains an undefined mixture of different soluble proteins and growth factors which supports the survival and proliferation of cells. For regulatory reasons, however, the use of non-definable additions such as serum is increasingly less tolerated, partly because of the risk of infection with bovine viruses. Totally serum-free production of cell lines is therefore the state of the art from a regulatory point of view.

Another possible solution is to carry out a "limited dilution" for the recloning. As this method only leads statistically to the production of single cell clones but many clones may also grow in one well, this process has to be repeated several times (usually 2-3 times) to ensure that the cell line obtained really does originate from only a single clone. These repeated cycles involve high labour and time costs which have a negative effect on the costs and timelines required.

Another approach is the use of "feeder" cells. The name comes from the English word "feed" and refers to a co-cultivation with usually non-dividing cells which serve to supply the desired cells in the culture with nutrients and secreted growth factors. The recloning efficiency can be significantly increased by feeder cells.

In another approach, recombinant proteins are added to the recloning medium, to promote the survival and growth of the individually deposited cells. Examples of recombinant proteins used are insulin, insulin-like growth factor (IGF), epithelial growth factor (EGF) or human serum albumin (HSA). These additives are obtained as purified proteins or protein solutions and added to the medium. The disadvantages of this method are the costs, the dependency on the availability of the recombinant proteins and their instability. The disadvantages include, inter alia:

the need to store them at −70° C.,
freeze/thaw cycles lead to inactivation and therefore have to be avoided,
rapid loss of activity in solution under cultivation conditions.

The aim of the present invention is to increase the recloning efficiency in the serum-free FACS-based cloning of production cells.

SUMMARY OF THE INVENTION

The solution to this technical problem of the reduced recloning efficiency in serum-free, preferably chemically defined and/or insulin-free medium is obtained by the use of transgenic albumin or HSA-producing cells or by the use of medium conditioned by such HSA-producing cells. The HSA is thus not added to the medium from outside as a purified protein but rather is released directly into the recloning medium by living cells.

The following embodiments are possible:
1. Use of an HSA-producing cell to prepare conditioned medium for die depositing of single cells.
2. Use of HSA-producing cells as feeder cells. In contrast to the use of recombinant HSA which is added to the medium once, the feeder cells in the multiwell plate continuously produce HSA after the depositing of single cells and thus assist the growth of the deposited cells for a longer time than after a single addition of the recombinant protein.
3. Use of HSA-producing cells as host cells for producing biopharmaceuticals. The cells are thus enabled to promote their growth by the secretion of HSA autologously even in the absence of feeder cells and recombinant additives.

The highest recloning efficiency can preferably be obtained by a combination of these approaches, i.e. by the use of HSA-producing host cells and HSA-conditioned medium. Optionally and depending on the nature of the subsequent analysis process, feeder cells may be used in addition.

By the use of HSA-producing cells as host or feeder cells or media conditioners the recloning efficiency and hence the quantity of clones obtained can be increased significantly. This effect is observed even at concentrations of less than 200 mg/L HSA, even <100 mg/L in the cloning medium. The activity/effectiveness of secreted HSA on the recloning efficiency is thus significantly higher than that of recombinant HSA, which is usually added in concentrations of 400 mg/L to >2 g/L. A preferred embodiment is the use of HSA-producing cells in insulin-free medium. The positive influence of HSA-producing cells and/or their medium on the recloning efficiency is apparent both in the presence and absence of feeder cells in different media.

It is also apparent in different cell lines/cell types such as for example hamster and mouse cells, as well as human and various other cell systems.

The HSA-producing cells used may be both naturally HSA-producing cells (such as human liver cells) and also genetically altered cells of other species.

A preferred embodiment consists of transgenic HSA-producing production cell lines such as CHO, BHK, NS0, Sp2/0 or Per. C6-cells. A particularly preferred embodiment comprises HSA-producing CHO cells.

The method described here for increasing the recloning efficiency in serum-free media by the use of HSA-producing cells or medium conditioned thereby results in a more effective clone screening and thereby in a more efficient cell line development process.

In biopharmaceutical development, the primary goal of recloning is to identify high-producing cell clones. A higher recloning efficiency, through the broader base of clones obtained, and as a result of a normal distribution of the clones in terms of productivity, leads to a higher probability of obtaining high-producing cell clones.

As fewer cells have to be deposited in dishes at a higher recloning efficiency in order to obtain the same number of living cell clones, there is also a significant saving in both time and effort as well as costs as a result. The process step is thus more economical overall.

Moreover, the increased recloning efficiency forms the basis for the use of highly efficient automated clone screening methods (screening robot).

In systems of this kind there is generally no selection of individual wells in the microtitre plate, but all are measured equally, irrespective of whether they contain a living cell population or not. As a result of all the wells in the plate being analysed the number of clones examined increases in direct proportion to the number of emergent clones. A recloning efficiency of only 10% means that 90% of the wells are empty and therefore cannot supply any usable data but are still analysed. In terms of economy, this means that in 90% of cases time and money in the form of reagents are expended without any data being gained. Therefore the efficiency of high throughput automation systems for early clone selection increases proportionally with the number of clones obtained after the depositing of single cells.

Another advantage of the method described is that the addition of HSA-producing cells as host cells and/or medium conditioners increases the recloning efficiency to a point where there is no need for feeder cells.

On the one hand this reduces the effort involved in producing and pre-cultivating the feeder cells and at the same time increases the reproducibility of the single cell cloning. In addition it makes it possible to use technologies for visually detecting the number of living cells as a tool for clone analysis. As the amount of product in the culture medium is in linear correlation with the number of producing cells, the technological development seeks to detect both the amount of product and the number of cells, so as to determine from these the highest producing cell clones, i.e. the cell clones with the highest specific productivity.

As feeder cells are difficult to distinguish visually from the emergent production cells, they are also included in the visual determination of cell numbers, leading to an inaccurate calculation of the total number of cells and hence an imprecise determination of the important parameter of specific productivity. A process without feeder cells is therefore advantageous and represents a preferred embodiment.

Possible applications for the method described can be found particularly in the production of biopharmaceuticals.

The increase in the recloning efficiency in the generation of production cells for biopharmaceutical production leads to a higher probability of a highly-productive clone and hence an improved or accelerated product development.

The process also increases the economy of this step and also makes it possible to use high-throughput automated clone analysing techniques.

The addition of recombinant proteins to insulin-containing medium for the purpose of increasing recloning efficiency is indeed described in the prior art (WO2006047380). By contrast, however, the use of secreted albumin or HSA, or medium from albumin- or HSA-producing cells, is explicitly described in the present Patent Application as an alternative and superior possibility. The HSA is not added exogenously to the medium as a recombinant purified protein, but rather the HSA is secreted directly into the recloning medium by the albumin-transgenic cells.

HSA-producing CHO cells are indeed described in the literature, but there is no description of either the use of HSA-producing cells as host cells for the production of a protein other than HSA, or of their use as feeder cells or as medium conditioners for increasing the recloning efficiency.

DESCRIPTION OF THE FIGURES

Schematic representation of the possible embodiments of HSA-producing cells:
(1) for preparing conditioned medium
(2) as feeder cells
(3) use of HSA-producing cells as host cells for biopharmaceutical production, i.e. the cell that produces the protein of interest additionally secretes HSA and thereby promotes its own growth during recloning.

These possible applications may be combined in order to increase the recloning efficiency still further.

(B) Tabulated summary of the HSA concentrations measured in the above media. The recloning efficiency is at its maximum when medium conditioned for 2-5 days is used. It is significantly higher than when recombinant HSA is added to the medium, although the HSA concentrations measured in the conditioned medium are lower by a factor of 5-50. Any longer conditioning leads to a reduced recloning efficiency in spite of a higher HSA content in the medium.

(B) The influence of the addition of HSA-conditioned media to commercial medium (HyQ SFM 4 CHO medium). The graph shows the recloning efficiency in a medium different from that in (A) without the use of feeder cells. In this medium no individually deposited cell grows into a living culture in the medium without additives. A few cells survive thanks to the addition of recombinant HSA (500 mg/L, darkgrey bars). A higher recloning efficiency on the other hand is achieved by using conditioned medium of HSA-producing cells (light-grey bars). The bars are averages of 3-5 evaluated 96-well plates for each condition; error bars show the standard deviation.

A single cell from a cell population is deposited on either autologous CHO-DG44 feeder cells or transgenic HSA-producing feeder cells. The recloning efficiency using DG44-cells was set at 1. (black bar). The grey bar gives the relative increase in the recloning efficiency when HSA-producing feeder cells are used. The bars indicate the averages of 3 evaluated 96-well plates for each condition.

This shows the recloning efficiency in batches containing untransfected DG44 cells that have been deposited on autologous feeder cells (1 placed, black), when recloning an HSA-producing cell in the presence of DG44-feeder cells (grey). The combination, i.e. the depositing of an HSA-producing cell on HSA-transgenic feeder cells (white), leads to a further significant increase in the recloning efficiency. The Figure shows the averages of 3 evaluated 96-well plates, the error bars show the standard deviation.

The graph shows the efficiency of the recloning when recombinant HSA is added in the concentrations specified. The maximum efficiency was achieved in this experiment when 1000 mg/L recombinant HSA were added to the recloning medium; this value was set at 100% and the efficiencies measured for the other batches were recorded in relation thereto.

DETAILED DESCRIPTION OF THE INVENTION

Definitions

Before the more detailed description of the invention by means of the non-restrictive exemplifying embodiments that follow, it should be pointed out that the use of the indefinite article, for example "a" or "an" and the definite article, namely "the", includes both the singular and plural of the term in question, unless one of the two forms is explicitly ruled out and reference is made to a particular form (singular or plural). Thus, the term "a cell" automatically includes "a plurality of cells" as well, unless it is explicitly stated that only a single cell is meant. The singular is explicitly meant, for example, where "a" or "one" is supplemented by (1).

The term "insulin" denotes a growth factor that is secreted by pancreatic beta cells. Insulin is known to the skilled man. Human zinc insulin or recombinant insulin is frequently used in cell culture. The concentration of insulin can be measured in the culture medium using routine experiments such as a commercially obtainable insulin-specific ELISA.

The term "insulin-free" means that the culture medium does not contain any insulin, particularly any recombinant insulin and no insulin is added to it either.

Albumin is the most commonly occurring protein in the plasma. It is produced in the liver and contributes to maintaining osmotic pressure in the blood. Albumin binds to nutrients and metabolites and thus assists with their transportation.

The term "albumin" in the present invention denotes a polypeptide component which has the biological activity of albumin. Albumin generally denotes animal albumin, particularly a mammalian albumin such as for example human, bovine, equine, murine, rat-like and porcine albumin and albumin from birds such as chickens, in particular, etc. Preferably the albumin is human serum albumin (HSA). In the present invention the terms "HSA" and "albumin" are used synonymously, i.e. "HSA" refers both to human albumin and to albumins from other animal species. In the present invention a distinction is made explicitly between recombinant HSA which is added to the culture medium from outside, and "secreted HSA", which is released into the reclonig medium directly, i.e. without purification or separation, by living HSA-producing cells. When reference is made to albumin or HSA secreted directly into the cell culture medium by living albumin-transgenic cells, this means that albumin or HSA is not added from outside as a purified protein.

The production of recombinant HSA is well known in the prior art and can be carried out e.g. using genetically modified yeasts (U.S. Pat. No. 5,612,197). Recombinant HSA may be obtained commercially from various suppliers, for example from Sigma-Aldrich (Recombinant HSA, Cat. No. A-7223). This is purified protein which can be added to the cultivation medium.

The data of the present invention show that "secreted HSA" has a significantly higher activity/effectiveness than HSA, as it brings about a substantial increase in the reclonig efficiency at significantly lower concentrations.

The term "significantly lower concentration" means according to the present invention:
- a concentration which is at least two times lower compared with recombinant or purified albumin,
- a concentration which is at least five times lower compared with recombinant or purified albumin,
- an albumin concentration which is lower by at least factor 2 than that of a comparable culture mixture containing recombinant or purified albumin,
- an albumin concentration which is lower by at least factor 5 than that of a comparable culture mixture containing recombinant or purified albumin,
- an albumin concentration which is lower by at least a factor 2 to 100, 2 to 5, 5 to 100, 20 to 100, 5 to 10 than that of a comparable culture mixture containing recombinant or purified albumin,
- an albumin concentration of less than 200 mg/L, preferably less than 100 mg/L, particularly preferably less than 60 mg/L.

In contrast to recombinant HSA the secreted HSA is released by HSA-producing cells of a living culture directly into the reclonig medium. It may originate from three sources: (a) from HSA-producing cells of a preliminary culture used to prepare conditioned medium, (b) HSA-producing feeder cells, or (3) HSA-secreting host cells (if the individually deposited producing cells have been genetically modified such that they themselves secrete HSA).

The concentration of HSA can be determined by routine methods such as a commercially obtainable ELISA (e.g. "Human Albumin ELISA Quantitation Kit", Bethyl Laboratories, Montgomery, Tex.)

The term "albumin or HSA-transgenic cell", "albumin- or HSA-producing cell" or "albumin- or HSA-secreting cell" denotes any cell that releases an albumin into the medium. This may either be a cell that naturally secretes albumin (e.g. a liver cell) or a cell that has been genetically modified, for example by the introduction of an albumin- or HSA-expression construction, such that it expresses albumin or HSA and releases it into the medium. A preferred embodiment of the present invention consists of albumin- or HSA-producing mammalian cells, most preferably albumin- or HSA-producing rodent cells, particularly albumin- or HSA-producing CHO- or NS0-cells. The terms such as "albumin- or HSA-transgenic cell", "albumin- or HSA-producing cell" and "albumin- or HSA-secreting cell" specified are used interchangeably in the present application.

The "specific productivity" of a cell indicates the quantity of a particular protein that is produced by a cell per unit of time, i.e. that is released into the medium, in the case of secreted proteins. The specific productivity is calculated from the quotient of the concentration of the product in the medium (=titre, determined by ELISA, for example) and the number of producing cells present over the time span under consideration, also known as the "IVC" (integral of the number of living cells over time). The specific productivity is usually given in 'pcd' (=pg/cell*day=picograms of secreted protein per cell and per day)).

The term "cloning/reclonig", "clone/reclone" in connection with cell culture means a technique by means of which a cell population of identical cells can be obtained from an original cell. The term "cell cloning" or "single cell cloning" thus means a process wherein single cells can be identified and isolated from a cell pool with cells of different genotypes and then replicated to form a cell population consisting of a plurality of genetically identical cells. If the cells are deposited individually, i.e. only one (1) cell per culture vessel, and then expanded to form a cell population of identical cells, the process is "direct single cell cloning". If a number of cells are simultaneously deposited in a culture vessel, expanded to form a cell population and this is divided up into cell populations of identical cells by repeated dilution (=limited dilution), this is described as an "indirect cloning" method.

"Single clones" or "single cell clones" or "clones" for short are genetically identical cells which originate from one (1) single cell. A cell population consisting of identical cells of the same origin is consequently referred to hereinafter as a "monoclonal cell population". If during the cultivation of cells of the same origin there are spontaneous changes in the genome, for example mutations and/or translocations, the individual cells of this cell population are still regarded as identical cells for the purposes of the present invention, and the culture is regarded as a monoclonal cell population. By contrast, a pool of stably transfected cells (transfectants) are not cell clones of the same lineage, i.e. they are not a monoclonal cell population, even if genetically identical starting cells are transfected with an identical nucleic acid.

The term "subclones/subcultures" refers to different generations of cells which are produced from an original cell or original culture by single or multiple passaging of the dividing cells. The words "subclones/subcultures" are used, for example, when identical cells or cell cultures are cultivated and replicated over a number of generations.

The term "cloning efficiency" or "reclonig efficiency" is defined as the percentage of cells which survive, divide and form vital cell populations after being deposited. If for example in a cell sorting operation 100 cells are distributed over 100 culture vessels and if 25 of these 100 individually deposited cells grow to form cultures, the cloning efficiency is 25%.

By "effective or efficient recloning" is meant a cloning efficiency of at least 10%, preferably at least 20%, more preferably at least 30% and even more preferably at least 40%. According to a particularly preferred embodiment of the present invention the term effective recloning means cloning with an efficiency of at least 50%, preferably at least 60%, most preferably at least 70% and even more preferably at least 80%.

The term "capable of division/expandable" for the purposes of the present invention describes the potential of a cell/cell population to divide endlessly but at the least over 2, preferably 4, passages. This potential may for example be reduced or destroyed altogether by irradiation with $[^{137}]$Cs or by mitomycin C treatment.

The term "derivative/descendant" refers to cells which can be traced back genetically to a particular starting cell and are formed for example by subcultivation (with or without selection pressure) and/or generated by gene manipulation. Re-isolations of cells of the same cell type are also included in the term "derivative/descendant". Thus, for example, all CHO cell lines are derivatives/descendants of the hamster ovary cells isolated from *Cricetulus griseus* by Puck et al., 1958, regardless of whether they were obtained by subcultivation, re-isolation or gene manipulations.

The term "feeder cell" comes from the English word "feed" and refers to a co-cultivation with usually non-dividing cells which serve to supply the desired cells in the culture with nutrients and secreted growth factors. For the preparation, living cells are growth-arrested by irradiation with UV or gamma radiation or treatment with Mitomycin C. The resulting feeder cells live and produce and secrete growth factors but are unable to divide further.

The term "autologous feeder cell" means that both the feeder cell and the cell which is to be cultivated in the presence of this feeder cell are derived taxonomically from the same origin. If for example the cell to be cultivated is a hamster cell (subfamily Cricetinae), preferably a cell of the genus *Cricetulus* or *Mesocricetus*, for example a CHO or BHK cell, each feeder cell originally isolated from this subfamily is a feeder cell which is autologous to these hamster cells of the subfamily Cricetinae.

According to a preferred embodiment the term "autologous feeder cell" means that both the feeder cell and the cell which is to be cultivated were derived from the same genus taxonomically or were originally isolated from the same genus (cells from *Cricetulus* or *Mesocricetus*). If for example the cell to be cultivated is a hamster cell of the genus *Cricetulus* or *Mesocricetus*, preferably a CHO or BHK cell, each feeder cell originally isolated from the genus in question is an autologous feeder cell in the sense of this invention.

According to another preferred embodiment an autologous feeder cell is present if the feeder cell and the cell to be cultivated come from the same species, for example *Cricetulus griseus* or *Mesocricetus auratus*. According to a particularly preferred embodiment an autologous feeder cell is present if both the feeder cell and the cell to be cultivated come from the same species and have the same tissue tropism (e.g. ovarian cells from *Cricetulus griseus*—CHO cells).

According to a particularly preferred embodiment a feeder cell is an autologous feeder cell if both the feeder cell and the cell to be cultivated originate from the same basic cell, for example if both cells were originally CHO-DG-44 cells or descendants of these cells. According to another preferred embodiment the feeder cell confers the same resistances, e.g. to antibiotics, as the cell which is to be cultivated. This is particularly advantageous when the cell deposition is carried out in the presence of a selecting agent, e.g. an antibiotic.

In one aspect the present invention particularly describes the use of HSA-producing feeder cells for increasing the recloning efficiency. In a preferred embodiment, autologous HSA-producing feeder cells are used.

The term "limited dilution" denotes an alternative method of recloning. A cell suspension is serially diluted and the cells are then deposited in a microtitre plate in different numbers of cells per well. In wells with high numbers of cells, many or all of the cells will survive as the result of adequate secretion of autocrine growth factors. The fewer cells are seeded per well, the fewer cells survive, which means that the dilution can thus be adjusted so that statistically only one single cell per well survives and grows into a monoclonal line. As this method only leads statistically to the formation of single cell clones, but it is possible for several clones to grow in one well, this process has to be repeated several times (normally 2 to 3 times) in order to ensure that the cell line obtained really is from a single clone.

By the term "conditioned medium" is meant medium from a culture of living cells. The effect of the conditioned medium is based on its content of growth factors that have been secreted into the medium by the cells of the preliminary culture and have thereby "conditioned" it.

Accordingly, the term "medium-conditioning cells" or "medium conditioner" refers to cells that are used to prepare conditioned medium.

In one aspect the present invention describes the use of HSA-producing cells as medium conditioners, so that the conditioned medium thus obtained contains inter alia the HSA secreted by these cells.

The term "serum" denotes the cell-free component of the blood. Serum contains an undefined mixture of different soluble proteins and growth factors that assist the survival and proliferation of cells. For the cell culture, foetal calf serum (FCS) or bovine serum (FBS) are predominantly used. The usual concentration ranges are 10-20% FCS or FBS as an addition to the cultivation medium.

The term "serum-free" means culture media and also cultivation conditions which are characterised in that cells are grown in the absence of animal and/or human serum, preferably in the absence of any proteins isolated from serum, preferably in the absence of non-recombinantly produced proteins. Consequently, the term "cells adapted to serum-free conditions" means those cells which can be replicated in the absence of animal or human serum or serum proteins.

The term "protein-free" means that the culture medium does not contain any animal proteins; proteins isolated from bacteria, yeasts or fungi are not regarded as animal proteins.

The term "chemically defined" describes a cell culture medium which is serum-free, preferably also protein-free, and which consists of chemically defined substances. Chemically defined media thus consist of a mixture of predominantly pure individual substances. One example of a chemically defined medium is the CD-CHO medium produced by Messrs Invitrogen (Carlsbad, Calif., US).

The expression "a cell which may be cultivated in suspension" refers to cells which are adapted to growth in liquid cultures ("suspension cultures") and whose ability to adhere to the surfaces of vessels, for example cell culture dishes or flasks, has been restricted or lost. Cells which are adapted both to serum-free growth and to growth in suspension are referred to as "non-adherent cells adapted to serum-free medium". If feeder cells are prepared from such cultures, these cells are by definition "non-adherent feeder cells adapted to serum-free medium".

The term protein/product of interest refers to biopharmaceutically significant proteins/polypeptides comprising e.g. antibodies, enzymes, cytokines, lymphokines, adhesion molecules, receptors and the derivatives or fragments thereof. However, a protein/product of interest is not restricted to these examples. Generally, all polypeptides that act as agonists or antagonists and/or have a therapeutic or diagnostic use are significant or of interest. Other proteins of interest are for example proteins/polypeptides that are used to alter the properties of host cells within the scope of so-called "Cell Engineering", such as e.g. anti-apoptotic proteins, chaperones, metabolic enzymes, glycosylation enzymes, and the derivatives or fragments thereof, but are not restricted thereto.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity. In addition, the polypeptides may multimerise and form homo- and heteromers.

By recombinant proteins are meant proteins that are produced by recombinant expression in host cells. Such recombinant proteins are produced under the strictest conditions of purity in order to minimise the risk of contamination. Recombinant proteins are usually produced in suitable host cells such as e.g. yeast cells, animal cells or prokaryotic cells (*E. coli* or other bacterial strains) using an expression vector such as for example a plasmid, bacteriophage, naked DNA or a virus, to introduce the recombinant protein into the host cell. Recombinant proteins are usually commercially available in purified form as concentrated protein solutions or in powder form. Recombinant HSA is obtainable for example from various commercial suppliers such as Sigma Aldrich.

Examples of therapeutic proteins are insulin, insulin-like growth factor, human growth hormone (hGH) and other growth factors, receptors, tissue plasminogen activator (tPA), erythropoietin (EPO), cytokines, e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN)-alpha, -beta, -gamma, -omega or -tau, tumour necrosis factor (TNF) such as TNF-alpha, -beta or -gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov et al., 1999). The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')2 fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cysteine groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described, cf. for example Huston et al., 1988.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted bisulphite bridges. Examples of diabodies can be found in the literature, e.g. in Perisic et al., 1994.

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al., 1996.

The term triabody is used in the art to denote a trivalent homotrimeric scFv derivative (Kortt et al., 1997). The direct fusion of VH-VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric coiled coil structures (Pack et al., 1993 and 1995; Lovejoy et al., 1993).

The term "antibody fusion" or "antibody fusion protein" denotes the fusion/coupling of a protein to an antibody or part of an antibody. In particular these include fusion proteins produced by genetic engineering, in which a therapeutic protein is coupled to the Fc part of an antibody, in order to increase the half-life/stability of the protein in the serum. The term also encompasses antibody fusions consisting of a peptide and an antibody or part of an antibody.

Preferred host cells for the purposes of the invention are hamster cells such as BHK21, BHK TK$^-$, CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are myeloma cells from the mouse, preferably NS0 and Sp2/0 cells and derivatives/descendants of these cell lines.

Examples of hamster and mouse cells which can be used according to the invention are given in Table 1 that follows. However, derivatives and descendants of these cells, other mammalian cells including but not restricted to cell lines of humans, mice, rats, monkeys, rodents, or eukaryotic cells, including but not restricted to yeast, insect, bird and plant cells, may also be used as host cells for the production of biopharmaceutical proteins.

TABLE 1

Known production cell lines

| Cell line | Accession number |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO-K1 | ATCC CCL-61 |
| CHO-DUKX (= CHO duk⁻, CHO/dhfr⁻) | ATCC CRL-9096 |
| CHO-DUKX B1 | ATCC CRL-9010 |
| CHO-DG44 | Urlaub et al., Cell 33[2], 405-412, 1983 |
| CHO Pro-5 | ATCC CRL-1781 |
| Lec13 | (Stanley P. et al, 1984). |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| Per. C6 | (Fallaux, F. J. et al, 1998) |
| CHL | ECACC No. 87111906 |

According to the invention, recombinant mammalian cells, preferably rodent cells, most preferably murine cells such as NS0 and hamster cells such as CHO or BHK are particularly preferred.

According to the invention the host cells are preferably established, adapted and cultivated totally under serum-free conditions. Particularly preferably the host cells are additionally established, adapted and cultivated totally in a medium that is not only serum-free but also free from any animal proteins/peptides.

Examples of suitable nutrient solutions include commercially obtainable media such as Ham's F12 (Sigma, Deisenhofen, DE), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S (Invitrogen), serum-free CHO-Medium (Sigma) and protein-free CHO-Medium (Sigma).

The term "production cell" or "producer cell" or "production clone" denotes a cell that is used in a process for preparing a protein. In particular this includes genetically modified cells that are used for the industrial production of recombinant proteins. Within the scope of this invention, the term includes in particular genetically modified eukaryotic host cells which express a recombinant protein and are used to prepare this protein. This includes in particular monoclonal cell lines for the production of therapeutic proteins.

The invention describes a method of cultivating a single cell comprising the following steps: (a) cultivating a cell population, (b) isolating a single cell from the said cell pool and (c) cultivating the said single cell in a conditioned medium, i) which contains albumin, preferably human serum albumin (HSA), which is secreted by living albumin-transgenic cells directly into said medium. In a specific embodiment the present invention describes a process in which the albumin secreted by living albumin-transgenic cells has the same effect on the recloning efficiency as recombinant or purified albumin at a concentration that is significantly lower. The invention describes in particular a process for cultivating a single cell, comprising the following steps: (a) cultivating a cell population, (b) isolating a single cell from said cell pool and (c) cultivating the said single cell in a conditioned medium, i) which contains albumin, preferably human serum albumin (HSA), which is secreted by living albumin-transgenic cells directly into said medium, ii) the albumin secreted by living albumin-transgenic cells achieving the same effect on the recloning efficiency as recombinant or purified albumin at a significantly lower concentration.

In a specific embodiment the present invention describes a process in which the albumin secreted by living albumin-transgenic cells has the same effect on the recloning efficiency as recombinant or purified albumin at a concentration that is at least two times lower. In a preferred embodiment, the present invention describes a process in which the albumin secreted by living albumin-transgenic cells has the same effect on the recloning efficiency as recombinant or purified albumin at a concentration that is at least five times lower. In a specific embodiment the present invention describes a process in which the albumin concentration in i) is lower by a factor of at least 2, preferably at least 5, than that of a comparable culture mixture containing recombinant or purified albumin. In another specific embodiment, the present invention describes a process in which the single cell in step (b) and (c) expresses a protein of interest.

In a preferred embodiment step c) is carried out under serum-free conditions, preferably using chemically defined and/or insulin-free medium. In a specific embodiment the present invention describes a process in which in step (c) albumin is present in a concentration of less than 200 mg/L, preferably less than 100 mg/L, particularly preferably less than 60 mg/L. In another specific embodiment the present invention describes a process in which albumin in step (c) ii) is present in a concentration that is lower by a factor of 2 to 100, 2 to 5, 5 to 100, 20 to 100 or 5 to 10, preferably at least in a concentration that is lower by a factor of 5, most preferably at least in a concentration that is lower by a factor of 10.

In a preferred embodiment the present invention describes a process wherein in step (c) the cell supernatant of living albumin-transgenic cells is added, which is removed between cultivation days 1 to 4. In a particularly preferred embodiment the present invention describes a process wherein in step (c) the cell supernatant of living albumin-transgenic cells is added which is removed on cultivation day 2. In another specific embodiment the present invention describes a process wherein the cell supernatant is taken from a cell culture with 1 to 4 million, preferably 1 to 2 million albumin-transgenic cells/ml. In a preferred embodiment of the invention the cell supernatant is taken from a cell culture with 1 to 4 million, preferably 1 to 2 million albumin-transgenic cells/ml and the albumin concentration in i) is lower than that of a comparable culture mixture containing recombinant or purified albumin by a factor of at least 5 to 10, preferably by a factor of at least 10.

In another preferred embodiment the present invention describes a process wherein the conditioned medium in step c) is produced by the addition of living albumin-transgenic feeder cells. Preferably, at most 50 0000 albumin-transgenic feeder cells/ml are added. Also preferred is a process according to the invention in which the albumin-transgenic feeder cells remain in the medium of step c) continuously for a period of at least 2 weeks. In a preferred embodiment of the invention the conditioned medium in step c) is produced by the addition of living albumin-transgenic feeder cells, in which 50 0000 albumin-transgenic feeder cells/ml or less are added and the albumin concentration in i) is lower that that of a comparable culture mixture containing recombinant or purified albumin by a factor of at least 5 to 100, preferably by a factor of 20 to 100 (preferably also be a factor of more than 100).

In another preferred embodiment the present invention describes a process wherein the conditioned medium in step (c) is produced by the fact that the single cell from step (b) and (c) is an albumin-transgenic cell. In a particularly preferred embodiment the single cell is transgenic both for albumin and for a gene of interest and the single cell produces both albumin and also at the same time a protein of interest. In a specific embodiment the present invention describes a process wherein in step c)
 a) living albumin-transgenic feeder cells are added or
 b) the cell supernatant of living albumin-transgenic cells, which is removed between days 1 and 4 of cultivation, preferably on day 2 of cultivation, is added.

The invention also describes a cell which is generated according to one of the processes according to the invention.

The invention further describes a process for producing a protein of interest in a cell, preferably a CHO cell, preferably under serum-free cultivation conditions, comprising the following steps:
 a) producing a cell population that contains a gene of interest that codes for a protein of interest,
 b) cultivating these cells under cultivation conditions that permit growth of the cells,
 c) isolating and depositing a single cell in a vessel, e.g. in a 96-well plate,
 d) cultivating the said single cell in conditioned medium in the presence of
   a) cell supernatant of living albumin-transgenic cells, which is taken between the days 1 and 3 of cultivation, preferably on day 2 of cultivation, or
   b) living albumin-transgenic feeder cells,
 e) selecting a cell corresponding to its expression level of the protein of interest,
 f) harvesting the protein of interest, for example by separating the cell components from the supernatant, and
 g) purifying the protein of interest.

In a specific embodiment the present invention describes a process, characterised in that the protein of interest is a recombinant protein, preferably a therapeutic protein, preferably an antibody or an antibody fusion protein or an antibody fragment.

In a specific embodiment the present invention describes a process, characterised in that the single cell is a hamster or murine cell, preferably a mouse myeloma cell, particularly preferably a CHO or BHK cell or an NS0 cell. In another specific embodiment the present invention describes a process, characterised in that the living albumin-transgenic cell comes from the same species as the individually deposited cell. Preferably, the cell is a "Chinese Hamster Ovary" (CHO) cell. More preferably, the cell is a hamster or murine cell, preferably a mouse myeloma cell, particularly preferably a CHO or BHK cell or an NS0 cell, depending on the species of the individually deposited cell.

In a particular embodiment the present invention describes a process, characterised in that it relates to autologous albumin-transgenic cells or feeder cells.

In another particular embodiment the present invention describes a process, characterised in that the isolation of a single cell in step b) is carried out by "limited dilution" or using a "fluorescence activated cell sorting" (FACS) apparatus.

In a preferred embodiment the present invention describes a process, characterised in that the cell in step (b) and (c) expresses a protein of interest. In particular the protein of interest is a therapeutic protein, preferably an antibody, an antibody fusion protein or an antibody fragment.

The invention also describes a protein which is prepared by a process described according to the invention.

The invention further describes a process for selecting a production cell, using a process according to the invention.

The invention further describes the use of a production cell according to the invention for biopharmaceutical protein preparation.

The invention further describes a serum-free conditioned culture medium that makes it possible to cultivate a single cell, containing:
 a) cell supernatant of living albumin-transgenic cells, which is taken between days 1 and 4 of cultivation, preferably on day 2 of cultivation, or
 b) living albumin-transgenic feeder cells for conditioning the medium.

Preferably, the medium according to the invention contains an albumin concentration of less than 200 mg/L, more preferably less than 100 mg/L, particularly preferably less than 60 mg/L. Preferably, autologous feeder cells are used. In a preferred embodiment the present invention describes a medium, characterised in that the single cell cultivated therein is a CHO cell. Particularly preferably this single cell expresses a protein of interest.

For putting the present invention into practice, unless stated otherwise, conventional techniques that are generally known to the skilled man from cell biology, molecular biology, cell culture, fermentation technology, etc. are used. The following experimental data are illustrative by nature and are not restrictive.

Experimental Section

Equipment and Methods

Cultivation of the Cells

The cells CHO-DG44/dhfr$^{-/-}$ (Urlaub et al., 1983) are permanently cultivated as suspension cells in serum-free HyQ SFM 4 CHO medium (HyClone) supplemented with hypoxanthine and thymidine or BI's own medium in cell culture flasks at 37° C. in a damp atmosphere and 5% $CO_2$. The cell counts and viability are determined with a CEDEX Cell Counter (Innovatis, DE) or by tryptan blue staining and the cells are then seeded in a concentration of $1\text{-}3\times10^5$/mL and run every 2-3 days. Recombinant CHO-DG44 are used for the single cell cloning. The cultivation of cloned recombinant cells is carried out analogously to these cells. Again, HyQ medium, Ex-Cell medium (JRH, USA) or BI's own medium without hypoxanthine and thymidine is used as the medium.

The cells NS0 can be permanently cultivated as suspension cells in serum-free hybridoma medium, animal component-free medium (Sigma, Aldrich, St. Louis, USA) in cell culture flasks at 37° C. in a damp atmosphere and 5% $CO_2$. The cell counts and viability can be determined with a CEDEX Cell Counter (Innovatis, DE) or by tryptan blue staining and the cells are then seeded in a concentration of $1\text{-}3\times10^5$/mL and run every 2-3 days.

Preparation of Feeder Cells by Irradiation

Suspended CHO-cells (untransfected cells) growing without serum and protein are centrifuged at 180 g for 10 minutes and adjusted to a cell concentration of $1\times10^6$/mL in HBSS (Hank's balanced salt solution).

Then the cells are irradiated with a radioactive irradiation source (Cs137-irradiator, Gammacell 2000, made by Molsgaard Medical A/S, Denmark) with an energy dose delivery of 4 Gy/min. After the irradiation the cells are seeded with about 10000 cells per well in 96-well microtitre plates in the Ex-Cell medium (JRH, USA) specific for the cells or BI's own medium (e.g. TH-9) and stored at about 37° C. and 5% $CO_2$ in an incubating chamber atmosphere.

HSA-producing feeder cells are produced in the same way.

The process is carried out accordingly with NS0 cells, while the feeder cells are kept/seeded in the particular medium specific for the cells.

Preparation of Conditioned Medium

The conditioned medium is obtained from the supernatant of an animal cell culture. The cells are put in at a sufficient seeding density and cultivated for 1-7 days. The supernatant is separated from the cells by centrifugation and then sterile-filtered. The filtrate obtained is used as the conditioned medium.

Determination of the has Concentration by ELISA

The HSA concentration is determined using the Human Albumin ELISA Quantitation Kit made by Bethyl (Cat.-No. E80-129) according to the manufacturer's instructions.

FACS-Based Cell Deposition

The automatic cell deposition (single or multiple cell deposition) is carried out with a Flow Cytometer (Coulter EPICS Altra (Messrs. Beckman-Coulter, Miami, Fla., USA) fitted with an argon laser (488 nm) using an Autoclone unit. The cells are centrifuged off in the exponential growth phase and taken up in buffer until the required cell concentration is obtained. Then the cells are sorted using the "Hypersort Option" at a speed of 8000-12000 cells/second according to their position in the scattered light. Cells that express a fluorescent protein may alternatively be sorted according to their fluorescence intensity in relation to the intracellularly expressed fluorescence protein. The cells are each individually deposited in 96-well microtitre plates (optionally) provided with feeder cells. During the sorting of CHO cells the cells are deposited in Ex-Cell medium (JRH, USA) or BI's own medium with the corresponding supplements of HSA and preferably IGF or insulin.

For NS0 cells the cell deposition is carried out accordingly in hybridoma medium, animal component-free medium (Sigma, Aldrich, St. Louis, USA).

Calculating the Recloning Efficiency

The recloning efficiency is calculated from the quotient of positive wells per plate to total number of wells per plate. The definition of positive wells is those in which there is exactly one clone.

EXAMPLES

Example 1

Preparation of HSA-Producing CHO-Cells

CHO-DG44 cells growing serum-free in suspension (Urlaub and Chasin, 1980) are transfected with a plasmid which carries an expression cassette for human serum albumin (HSA) and DHFR as selectable markers. Stably transfected HSA-cell pools are produced by subsequent cultivation in HT-free medium. Using an HSA-specific ELISA those pools that secrete most HSA are selected. They are subjected to gene amplification by cultivation in the presence of methotrexate (MTX). By subsequent Limited Dilution HSA-producing cell lines are prepared from the initially heterogeneous cell population and these cells lines are in turn tested for their specific HSA-productivity. These lines are substantially to a further round of gene amplification by cultivation in medium with an elevated MTX concentration, so as to increase the HSA secretion rate further. As MTX can also leads to an reduction in cell growth at the same time, the cell lines obtained are subsequently investigated both for their increased productivity and for their growth properties and the cell line with the highest productivity and good growth is selected. From this cell a cell bank is produced which can be accessed in all future experiments.

Example 2

Increasing the Recloning Efficiency by the Use of Conditioned Medium from HSA-Producing Cells One possible embodiment of the present invention consists in the use of HSA-producing cells to increase the recloning efficiency. Before the recloning a culture of HSA-producing cells is started which condition the culture medium over several days, i.e. release growth factors and especially the HSA secreted by them into the medium. On the day of the recloning this conditioned medium is separated from the living HSA-producing cells by centrifugation, filtered (optionally) and added to the recloning medium in a ratio of 1:1.

In order to determine the optimum duration of the media conditioning, conditioned medium is obtained from a 2, 3, 4, 5, 6 and 7 day old culture and used for the recloning experiment. The positive control used is fresh medium to which 500 mg/L of purified recombinant HSA has been added.

Figure 1:
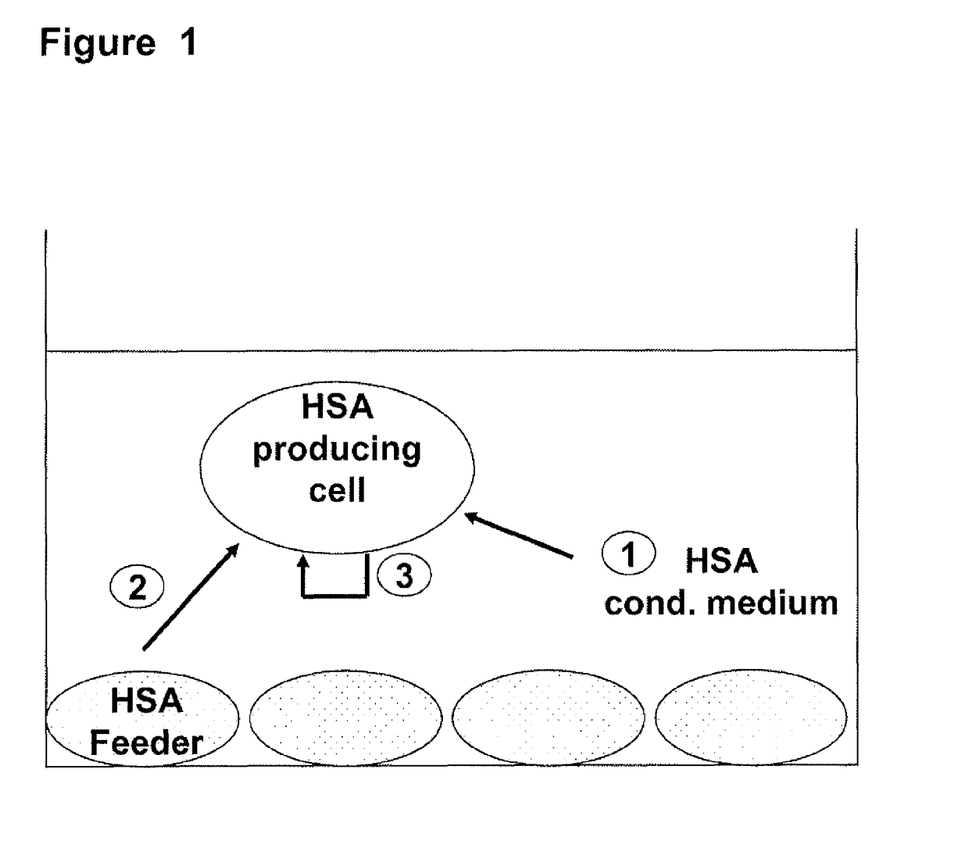
FIG. 1: POSSIBLE APPLICATIONS OF THE INVENTION
Figure 2:
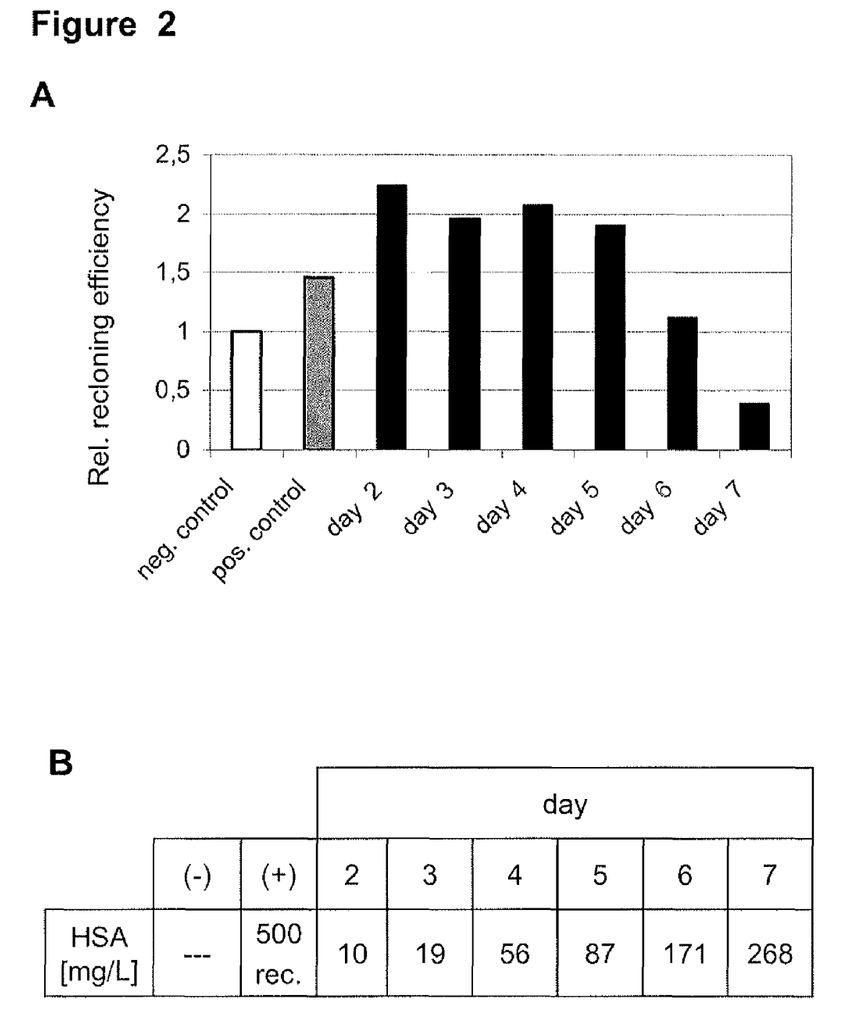
FIG. 2: PREPARATION OF CONDITIONED MEDIUM OF HSA-PRODUCING CELLS IN ORDER TO INCREASE THE RECLONING EFFICIENCY (A) This shows the relative recloning efficiency when using fresh recloning medium without any additions (negative control, white) and the relative increase in recloning by the addition of 500 mg/L recombinant HSA (positive control, grey) or 50% conditioned medium from a culture of HSA-producing cells, which is removed from the culture after the stated number of days and added (black bars).

As can be seen in FIGS. 2A, B, the use of conditioned medium of HSA-producing cells leads to a significant increase in the efficiency of single cells deposition compared with the negative control. By the addition of recombinant HSA (positive control) the recloning efficiency is also increased, but not as much as by the medium of HSA-secreting cells that has been conditioned for 2-5 days. The HSA concentration in the conditioned medium increases continuously over time, yet the recloning efficiency decreases when medium is used that has been conditioned for longer than 5 days. Surprisingly, the greatest increase in efficiency is obtained by means of conditioned medium from day 2, 3 or 4, in which the HSA concentration of 10 to about 60 mg/L is much lower than the concentration of recombinant HSA used in the positive control. This shows that the secreted HSA is active even at low concentrations and compared with recombinant HSA has an effectiveness that is 5 to 50 times higher in relation to the increase in recloning efficiency.

Example 3

Increase in Recloning Efficiency in Different Media

Figure 3:
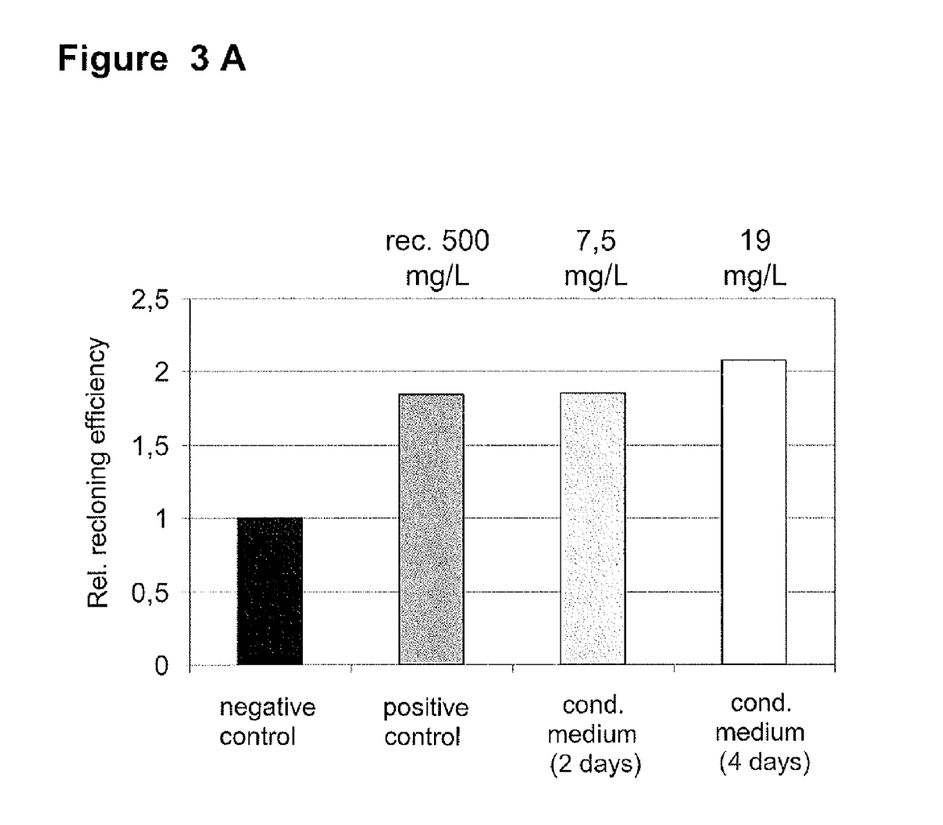
FIG. 3: INCREASE IN THE RECLONING EFFICIENCY AS A RESULT OF THE USE OF HSA-CONDITIONED MEDIUM (A) The influence of HSA-conditioned medium in the presence of feeder cells. This Figure shows the relative recloning efficiency of cells that are individually deposited on 10,000 growth-arrested feeder cells. The negative control shows the recloning efficiency in Boehringer's own medium without any additions (here set at 1), while in the positive control 500 mg/L recombinant HSA had been added to the medium. As a result of the use of conditioned medium of a 2 to 2 old culture of HSA-producing cells the recloning efficiency can be increased still further. The HSA-concentrations measured in this medium are shown above the bars.

In order to test whether the observed increase in recloning efficiency by using conditioned medium from HSA-producing cells operates independently of the medium, single cells are recloned in different media: In one batch the single cell is deposited in BI's own medium in the presence of CHO-DG44 feeder cells (FIG. 3A), and in another it is deposited in a commercial medium without feeder cells (FIG. 3B).

In both media, the use of the conditioned medium from HSA-secreting cells leads to a significant increase in recloning efficiency, which is both higher than in the negative control than in the positive control, wherein recombinant HSA was added to the recloning medium. In the batch without feeder cells in commercial medium no cells survive in the negative control, but by using the conditioned medium of HSA-producing cells a 5-13% recloning efficiency can be achieved.

In both experiments it is shown again that the secreted HSA from the conditioned medium acts at significantly lower concentrations and is hence more efficient than HSA added recombinantly to the medium.

Example 4

Increase in the Recloning Efficiency as a Result of HSA-Producing Feeder Cells

Conditioned medium from a preliminary culture of HSA-producing cells is added to the recloning medium once before the individually deposited cells are seeded. These cells thus receive HSA-containing medium only once at the beginning during the three-week phase of emergence after recloning. HSA-producing feeder cells could by contrast supply the emergent single cell clones continuously with HSA.

In order to investigate whether the use of HSA-producing feeder cells leads to a further increase in recloning efficiency, CHO-DG44 cells are deposited singly in four 96-well plates with HSA-producing and non-HSA-producing feeder cells. As in the previous example, the recloning medium contains 50% conditioned medium from an HSA-producing preliminary culture. After three weeks the emergent monoclonal cell colonies in each cell culture plate are counted and the recloning efficiency is calculated.

Figure 4:
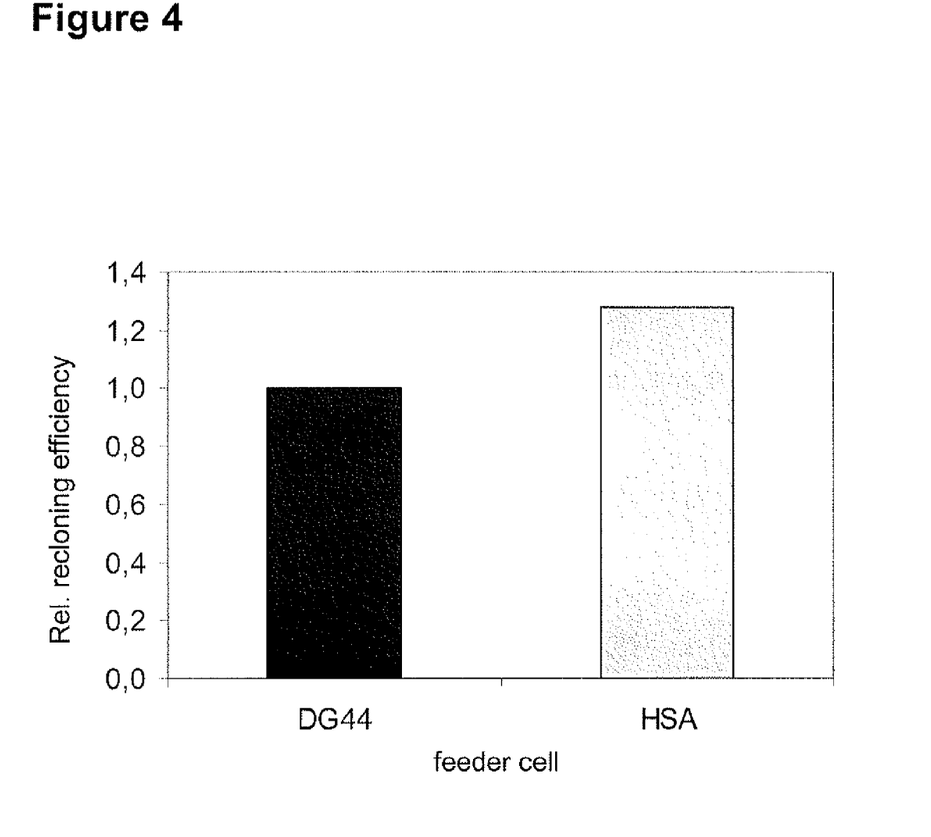
FIG. 4: INCREASE IN RECLONING EFFICIENCY BROUGHT ABOUT BY HSA-PRODUCING FEEDER CELLS

As shown in FIG. 4, the recloning efficiency when using HSA-producing feeder cells is significantly higher than in the plates containing normal feeder cells. The increase is about 25%. Accordingly, by combining HSA-conditioned medium and HSA-producing feeder cells it is possible to achieve another significant increase in the recloning efficiency.

Example 5

HSA-Producing Host Cells Show an Increased Recloning Efficiency

Another possible way of increasing the recloning efficiency might be to use HSA-producing host cells to produce a therapeutic protein. In this way during the recloning the individually deposited producer cells could themselves produce HSA and stimulate themselves via an autocrine loop. To check whether this process actually leads to increased recloning efficiencies, both normal CHO-DG44 cells and HSA-producing cells are individually seeded onto DG44- and HSA-producing feeder cells. After three weeks, the emergent colonies are counted and the recloning efficiency for all three batches is calculated.

Figure 5:
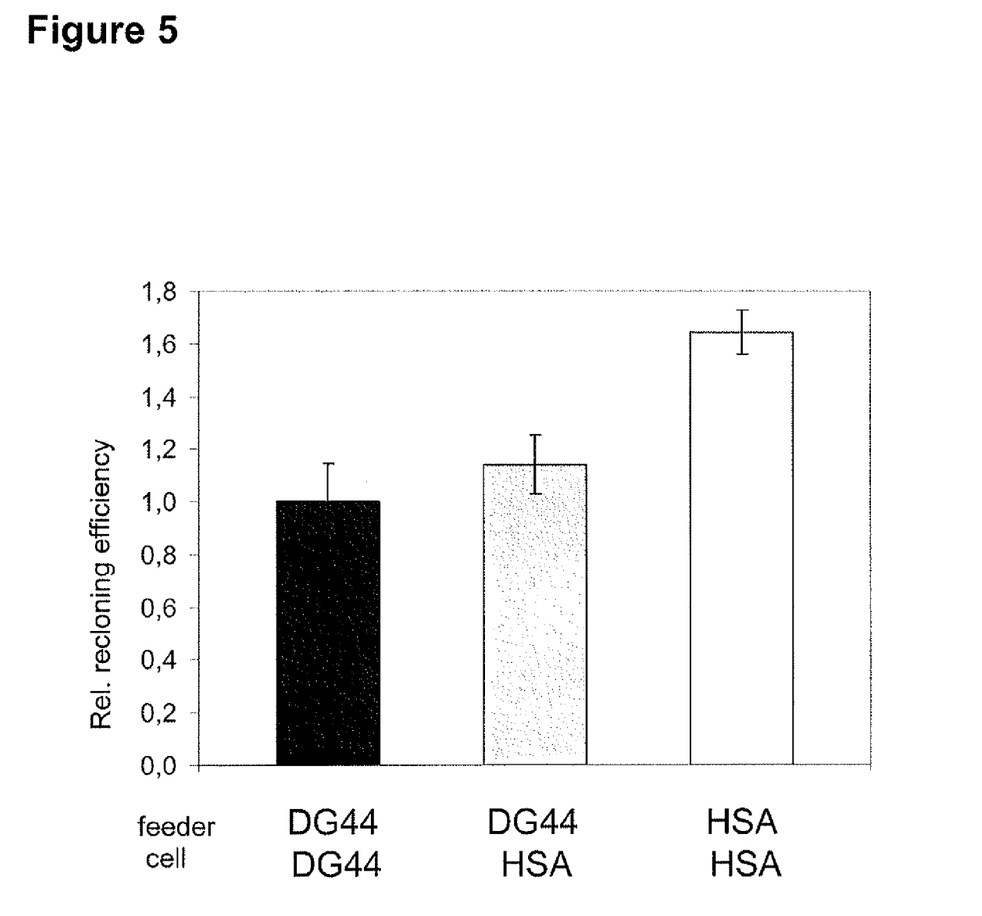
FIG. 5: COMBINATION OF HSA-PRODUCING FEEDER AND HOST CELLS
Figure 6:
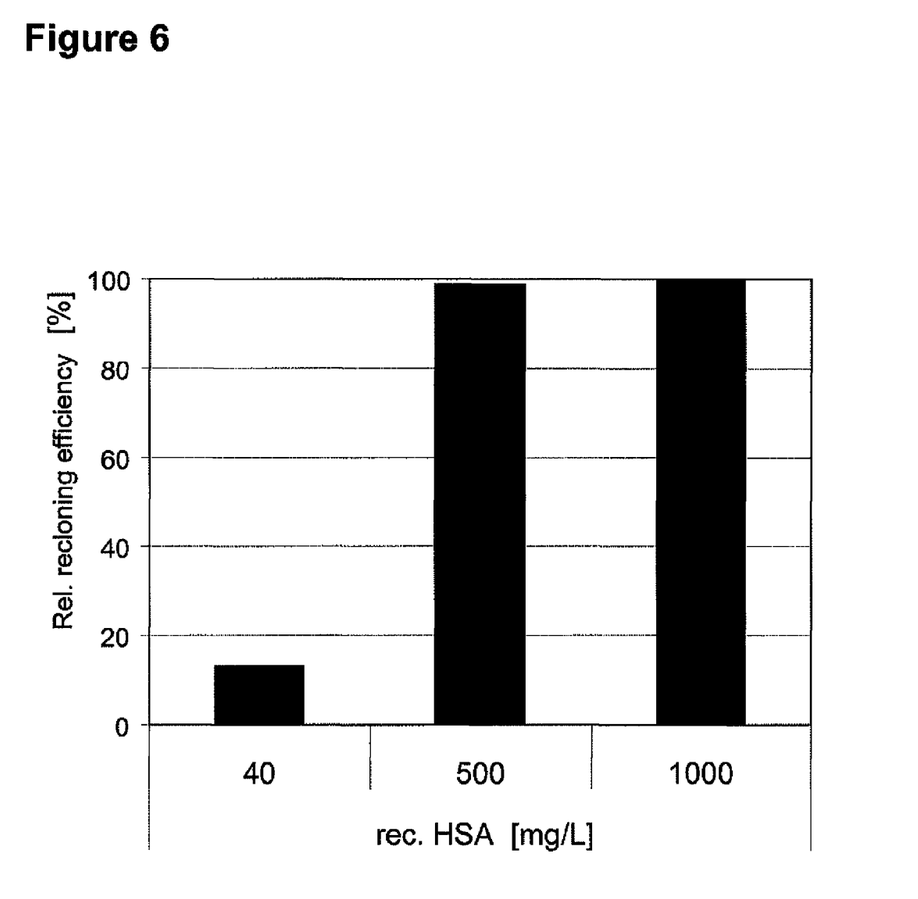
FIG. 6: CONCENTRATION-DEPENDENT INCREASE IN THE RECLONING EFFICIENCY AS A RESULT OF THE ADDITION OF RECOMBINANT HSA

FIG. 5 shows that the recloning efficiency is lowest in the culture dishes with unaltered CHO-DG44 host and feeder cells. If on the other hand HSA-producing cells are recloned, more monoclonal colonies emerge straight away. This shows that the probability of an HSA-producing cell surviving recloning and forming a culture capable of replication is higher than that of a cell that does not secrete HSA.

The greatest increase in recloning efficiency is obtained by a combination in which an HSA-producing host cell is seeded on HSA-producing feeder cells. This mixture leads to a further increase in the recloning efficiency of more than 40%. Compared with the control mixture without HSA-producing feeder cells there may even be an increase of more than 50%.

Example 6

Increased Recloning Efficiency of NS0-Cells

The preceding experiments show that the recloning efficiency of hamster cells can be increased by means of secreted human serum albumin. These results would tend to indicate that HSA has a positive effect on recloning efficiency across species.

To test this hypothesis, murine NS0 hybridoma cells that produce a therapeutic protein are subjected to recloning. They are placed, firstly, in fresh medium, and secondly in medium to which conditioned medium from an HSA-producing CHO cell culture has been added and in a third batch on HSA-producing feeder cells. Compared with recloning in fresh medium or conditioned medium of a cell culture of non-HSA-secreting cells the use of HSA-producing cells has a positive effect on recloning efficiency. This applies both to the use of conditioned medium from HSA-secreting cells and also HSA-producing feeder cells.

This shows that human HSA which is secreted by hamster cells can assist the recloning of murine cells.

Example 7

Use of Secreted HSA Increases the Recloning Efficiency Of Human Cells

To set this finding on an even broader base, human HEK293-based production cells are recloned in the presence and absence of conditioned medium of HSA-producing cells.

Compared with recloning in fresh medium or conditioned medium of a cell culture of non-HSA-secreting cells the use of HSA-producing cells has a positive effect on the recloning efficiency. This applies both to the use of conditioned medium of HSA-secreting cells and also HSA-producing feeder cells.

It can be concluded from this that the effect of secreted HSA acts on the recloning efficiency of individually deposited cells of several species, i.e. the activity works across species.

Example 8

Increased Recloning Efficiency by HSA-Producing Cells Increases the Probability of the Identification of High-Producing Cells The level of the specific productivity of producer cells in a heterogeneous cell population is normal distributed. This means that most of the cells have an average productivity, while a few cells produce a large amount and only a very small percentage produce a very large amount of recombinant product. This fact explains the effort that is expended on cell screening and the identifying of high-producing cells in industrial cell line development programmes. It also means that the likelihood of finding these high producers is directly correlated with the recloning efficiency: the more cells emerge after recloning, the more likely it is that there will be a high-producing cell among them.

In order to verify this in practice, a heterogeneous population of stably transfected CHO producing cells which secrete a therapeutic protein is subjected to recloning. Some are placed in a recloning medium to which 50% conditioned medium from the parental CHO-DG44 cell has been added (batch 1), and some are placed in 50% conditioned medium from a culture of HSA-producing cells (batch 2).

As in the previous Examples, more cells grow into clonal cell lines in the batches in which medium from HSA-producing cells was used.

In the next step 100 clones were selected from the two recloning trials and their productivity was determined by product-specific ELISA. The distribution of the specific productivity over these 100 clones shows a normal distribution in both cases. In the 100 clones that had emerged from the cells that were recloned using medium from HSA-conditioned medium (batch 2), the mean value of this curve has shifted significantly to the right, towards higher productivities. The mean value of the productivity of the 10 highest-producing cells from this batch 2 is higher than that of the 10 highest cell lines from the recloning batch without HSA-producing cells (batch 1). Accordingly the cell line that is selected as the highest-producing clone for the production of the therapeutic protein comes from batch 2.

This confirms that more cells with higher productivities are indeed obtained from the recloning batch with HSA-producing cells, thus increasing the probability of identifying them. At the same time there is also a greater likelihood of finding the few cells that produce the recombinant protein product in very large amounts and thus make it possible to select and use a high-producing clone for the production.

The invention claimed is:

1. Process for cultivating a single cell, comprising the following steps:
    (a) cultivating a cell population to form a cell pool,
    (b) isolating a single cell from the said cell pool and
    (c) cultivating the said single cell in a conditioned medium obtained from the supernatant of an animal cell culture comprising living albumin-transgenic cells; and which supernatant contains albumin secreted by said living albumin-transgenic cells directly into said supernatant.

2. The process according to claim 1, wherein the albumin secreted by living albumin-transgenic cells in step c) achieves the same effect on the recloning efficiency as recombinant or purified albumin at a significantly lower concentration.

3. The process according to claim 1, wherein albumin in step (c) is present in a concentration of less than 200 mg/L.

4. The process according to claim 1, wherein in step (c) the living albumin-transgenic cells are cultivated for 1 to 4 days prior to use of the cell supernatant in the conditioned medium in step (c).

5. The process according to claim 4, wherein in step (c) the cell supernatant of living albumin-transgenic cells is cultivated for 2 days prior to its use in the conditioned medium in step (c).

6. The process according to claim 4, wherein the albumin-transgenic cell supernatant is taken from said animal cell culture with 1 to 4 million albumin-transgenic cells/ml.

7. The process according to claim 1, wherein the conditioned medium in step c) further comprises living albumin-transgenic feeder cells.

8. The process according to claim 7, wherein the amount of albumin-transgenic feeder cells added to the conditioned medium is at most 500,000 albumin-transgenic feeder cells/ml of conditioned medium.

9. The process according to claim 7, wherein the albumin-transgenic feeder cells remain in the medium of step c) continuously over a period of at least 2 weeks.

10. The process according to claim 1, wherein the conditioned medium in step (c) is produced by the fact that the single cell from step (b) and (c) is an albumin-transgenic cell.

11. The process according to claim 10, wherein in step c):
    a) the conditioned medium further comprises living albumin-transgenic feeder cells or
    b) the animal cell culture comprising living albumin-transgenic cells is cultivated between 1 and 4 days before the cell supernatant of living albumin-transgenic cells is used in the conditioned medium.

12. The process according to claim 1, characterised in that the single cell is a hamster or murine cell.

13. The process according to claim 1, characterised in that the living albumin-transgenic cell comes from the same species as the individually deposited cell.

14. The process according to claim 1, characterised in that the single cell in step (b) and (c) expresses a protein of interest.

15. The process according to claim 14 characterised in that the protein of interest is a therapeutic protein, an antibody fusion protein or an antibody fragment.

16. A process for producing a protein of interest in a cell, comprising the following steps:
    a) producing a cell population that contains a gene of interest that codes for a protein of interest,
    b) cultivating these cells under cultivation conditions that permit growth of the cells,
    c) isolating and depositing a single cell in a vessel,
    d) cultivating the said single cell in conditioned medium in the presence of
        i) a cell supernatant of living albumin-transgenic cells, which cell supernatant is taken from an animal cell culture comprising living albumin-transgenic cells between 1 and 3 days after cultivation of living albumin-transgenic cells, or
        ii) living albumin-transgenic feeder cells,
    e) selecting a cell corresponding to its expression level of the protein of interest,
    f) harvesting the protein of interest, and
    g) purifying the protein of interest.

* * * * *